(12) United States Patent
Hsiao

(10) Patent No.: US 8,765,073 B1
(45) Date of Patent: Jul. 1, 2014

(54) WALL SOCKET AROMA DIFFUSER USING AROMA CAPSULE

(71) Applicant: Ming Jen Hsiao, Road Town (VG)

(72) Inventor: Ming Jen Hsiao, Road Town (VG)

(73) Assignee: Serene House International Enterprise Ltd., Virgin Islands (VG)

( * ) Notice: Subject to any disclaimer, the term of this patent is extended or adjusted under 35 U.S.C. 154(b) by 0 days.

(21) Appl. No.: 13/710,640

(22) Filed: Dec. 11, 2012

(51) Int. Cl.
| A61L 9/00 | (2006.01) |
| A01G 13/06 | (2006.01) |
| A24F 25/00 | (2006.01) |
| A61L 2/00 | (2006.01) |
| A61L 9/012 | (2006.01) |
| A61L 9/03 | (2006.01) |

(52) U.S. Cl.
CPC .... *A61L 2/00* (2013.01); *A61L 9/00* (2013.01); *A61L 9/012* (2013.01); *A61L 9/03* (2013.01)
USPC .............................. 422/306; 392/386; 239/34

(58) Field of Classification Search
CPC ............. A61L 2/00; A61L 9/00; A61L 9/012; A61L 9/03
USPC .................. 422/5, 125, 306; 392/386; 239/34
See application file for complete search history.

(56) References Cited

U.S. PATENT DOCUMENTS

| 3,872,280 A * | 3/1975 | Van Dalen .................... 392/390 |
| 8,066,420 B2 | 11/2011 | Hsiao |
| 8,147,116 B1 | 4/2012 | Hsiao |
| 8,262,277 B2 | 9/2012 | Hsiao |
| 2006/0153744 A1* | 7/2006 | Thompson et al. ........... 422/122 |

* cited by examiner

*Primary Examiner* — Monzer R Chorbaji
(74) *Attorney, Agent, or Firm* — Chun-Ming Shih

(57) ABSTRACT

A wall socket aroma diffuser using an aroma capsule is provided, including a wall socket aroma diffuser having a transparent receiving unit and an aroma capsule received in the wall socket aroma diffuser. The aroma capsule is heated to diffuse scent, and is disposable after the aroma thereof is diffused into an ambient environment completely. It is thus easy, safe for a user to replace the used aroma capsule with a new one because the aroma capsule will not be broken and the aroma thereof will not flow to a region outside of the aroma capsule. The user does not need to wash the aroma diffuser. The wall socket aroma diffuser further includes a light emitting diode that emits and projects light onto the transparent receiving unit. The light is guided and diffused by the receiving unit to generate color that pleases people's eyes.

12 Claims, 4 Drawing Sheets

WALL SOCKET AROMA DIFFUSER USING AROMA CAPSULE

CROSS-REFERENCES TO RELATED APPLICATION

Two pending new application Ser. No. 13/543,490 and 13/549,493 filed on Jul. 15, 2012 are hereby incorporated by reference.

BACKGROUND OF THE INVENTION

1. Field of the Invention

This invention relates to aroma diffusers, and, more particularly, to an aroma diffuser using an aroma capsule.

2. Description of Related Art

A general aroma diffuser, disclosed in U.S. Pat. No. 8,066,420, U.S. Pat. No. 8,262,277 and U.S. Pat. No. 8,147,116, for example, includes a power source, a lamp, and essential oil or aroma wax. The essential oil and the aroma wax are likely to flow out of the lamp if the lamp is toppled. Therefore, a user has to provide a certain receiving unit for the essential oil and the aroma wax to be received therein. Accordingly, the user takes the aroma wax out from the receiving unit and place it a ceramic receiving tank above a hollow frame carefully, in order not to be contaminated by the aroma wax. The aroma wax is then heated. After the aroma wax evaporates completely, the user washes and cleans the receiving tank. If the receiving tank is not sufficiently clean, new aroma wax will mix with the previous one, and diffuses unexpected scent. If the receiving tank is made of a brittle material such as ceramic, the ceramic receiving tank is likely to be broken if it is not cleaned carefully.

The aroma diffuser also provides light that penetrates the receiving tank and reaches to a region outside of the receiving tank directly. Such direct light is harsh to people's eyes. Moreover, the aroma diffuser has a power plug that is stationary. Therefore, a user cannot adjust the power plug at his will.

SUMMARY OF THE INVENTION

In view of the problems of the prior art, the present invention provides a wall socket aroma diffuser using an aroma capsule. The aroma capsule is disposable after the aroma thereof evaporates completely. The aroma capsule is not broken. Therefore, it is easy and safe to replace the aroma capsule with a new one.

In an embodiment, a receiving unit of the wall socket aroma diffuser using the aroma capsule is made of a transparent material. A lamp emits and projects light onto the transparent receiving unit. The light is guided and diffused to generate color, and the color is displayed via a light guiding flange to an outer side of the wall socket aroma diffuser.

The wall socket aroma diffuser comprises a swing plug device. Therefore, the wall socket aroma diffuser can be plugged into a socket heading any direction and diffuses scent upward.

The present invention provides a wall socket aroma diffuser using an aroma capsule, including: a wall socket aroma diffuser including a housing, a receiving unit, a heat conducting member, an electrical heat source, and an electrical plug device, wherein the housing has a free end, the receiving unit is coupled to the free end of the housing and has an upper opening and a lower opening, the heat conducting member is coupled to the lower opening of the receiving unit, the electrical heat source is coupled to and disposed on a lower side of the heat conducting member, the electrical plug device is disposed on one side of the housing, and the electrical plug device is electrically connected to the electrical heat source; and an aroma capsule received in the upper opening of the receiving unit and being in contact with the heat conducting member, wherein the aroma capsule has a disposable container and aroma, the disposable container has an opening, and the aroma is received in the disposable container, wherein the electrical heat source is electrically connected to a power supply and generates and conducts heat to the heat conducting member, and the heat conducting member conducts the heat to the disposable container and the aroma for the aroma to diffuse scent.

In an embodiment, the aroma capsule includes an air ventilation film that covers the opening of the disposable container and the aroma received therein. A sealing cover is further coupled to the opening and the air ventilation film to seal the aroma wax in the disposable container and ensure the quality of the aroma wax. A user can easily lift off the sealing cover and place the aroma capsule in the receiving unit. The aroma capsule receives the heat generated by the electrical heat source to diffuse scent. If the aroma diffuser is toppled by chance, the aroma (e.g., aroma wax) is prevented by the air ventilation film from flowing to the aroma diffuser or a region outside of the aroma diffuser. Therefore, the wall socket aroma diffuser does not pollute the environment, and is safe to use. In an embodiment, the receiving unit is made of metal, and the aroma capsule is disposable. Therefore, the user does not need to wash and clean the receiving unit. In an embodiment, the electrical plug device can be plugged into a socket toward any direction, and the wall socket aroma diffuser can diffuse scent upward. In an embodiment, the receiving unit and the light guiding flange are made of a transparent material. Light will pass and be reflected by the transparent receiving unit, and is not harsh to people's eyes. The light, together with the aroma scent, provides a pleasant environment. The user can see the pleasant light and smell the fragrant aroma scent.

As compared with the aroma diffuser of the prior art, which involves an inconvenient, dangerous aroma block replacement process and a tiresome cleaning process, the present invention provides a wall socket aroma diffuser that brings temperament and interest to people's daily life. Therefore, people can relax themselves by seeing the non-harsh, pleasant light and smelling the fragrant aroma scent.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

Figure 1:
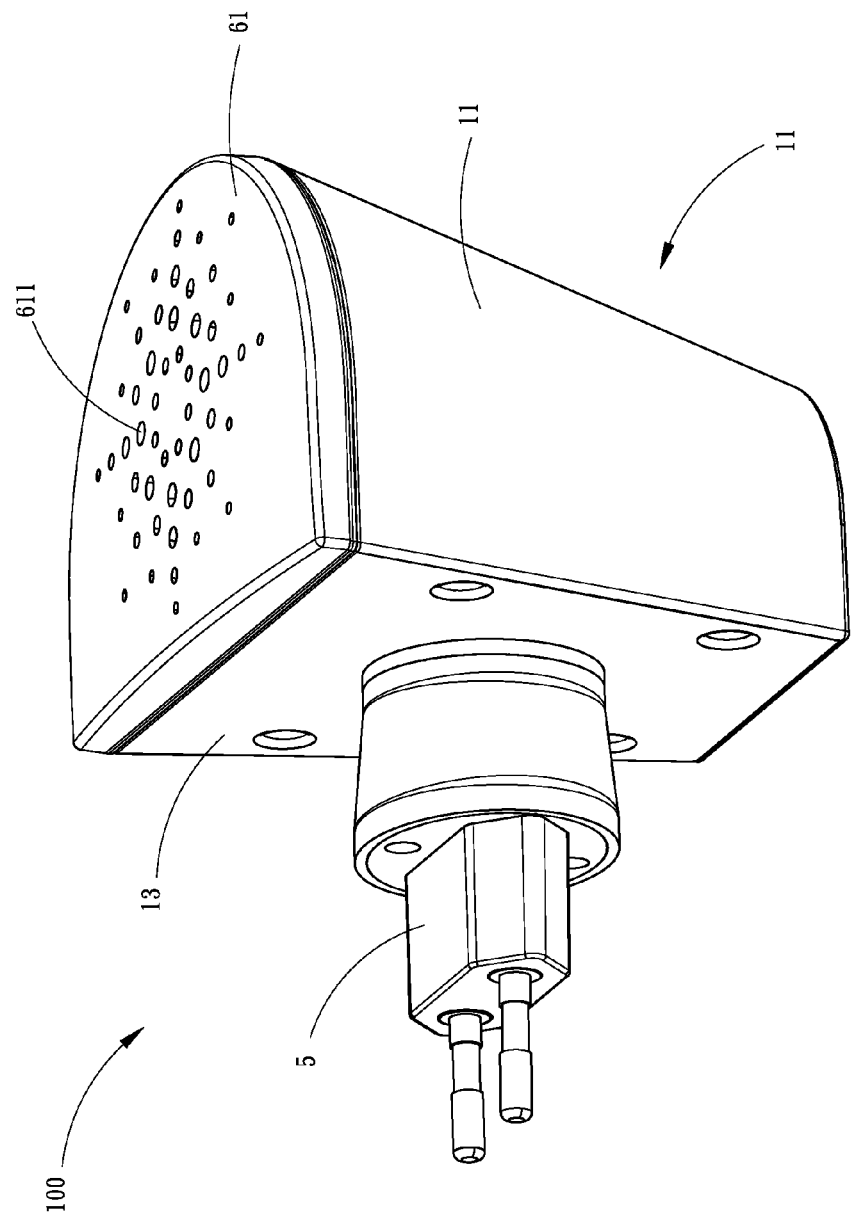
FIG. 1 is a schematic diagram of a wall socket aroma diffuser using an aroma capsule according to the present invention.
Figure 2:
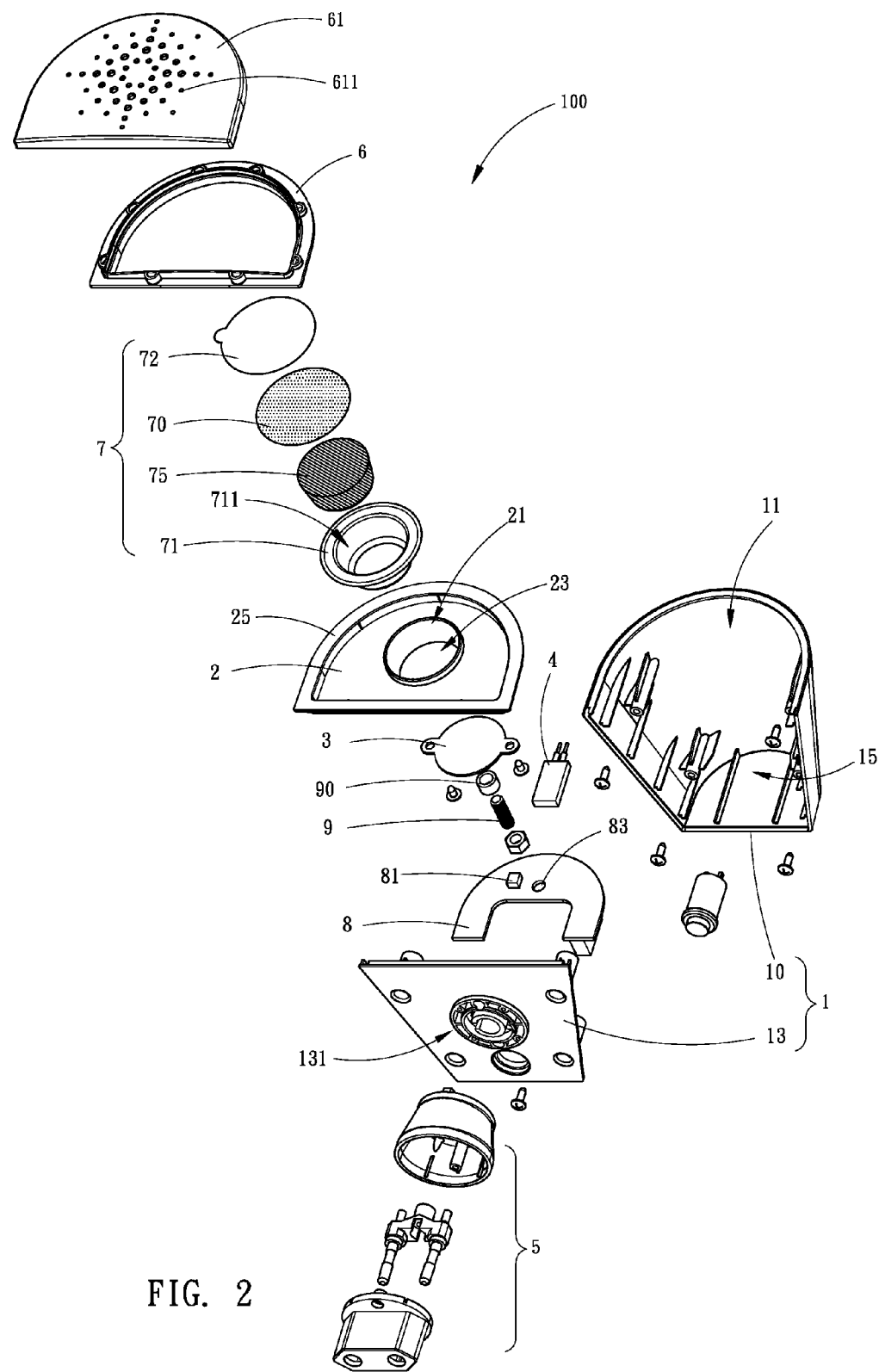
FIG. 2 is an exploded view of the wall socket aroma diffuser shown in FIG. 1.
Figure 3:
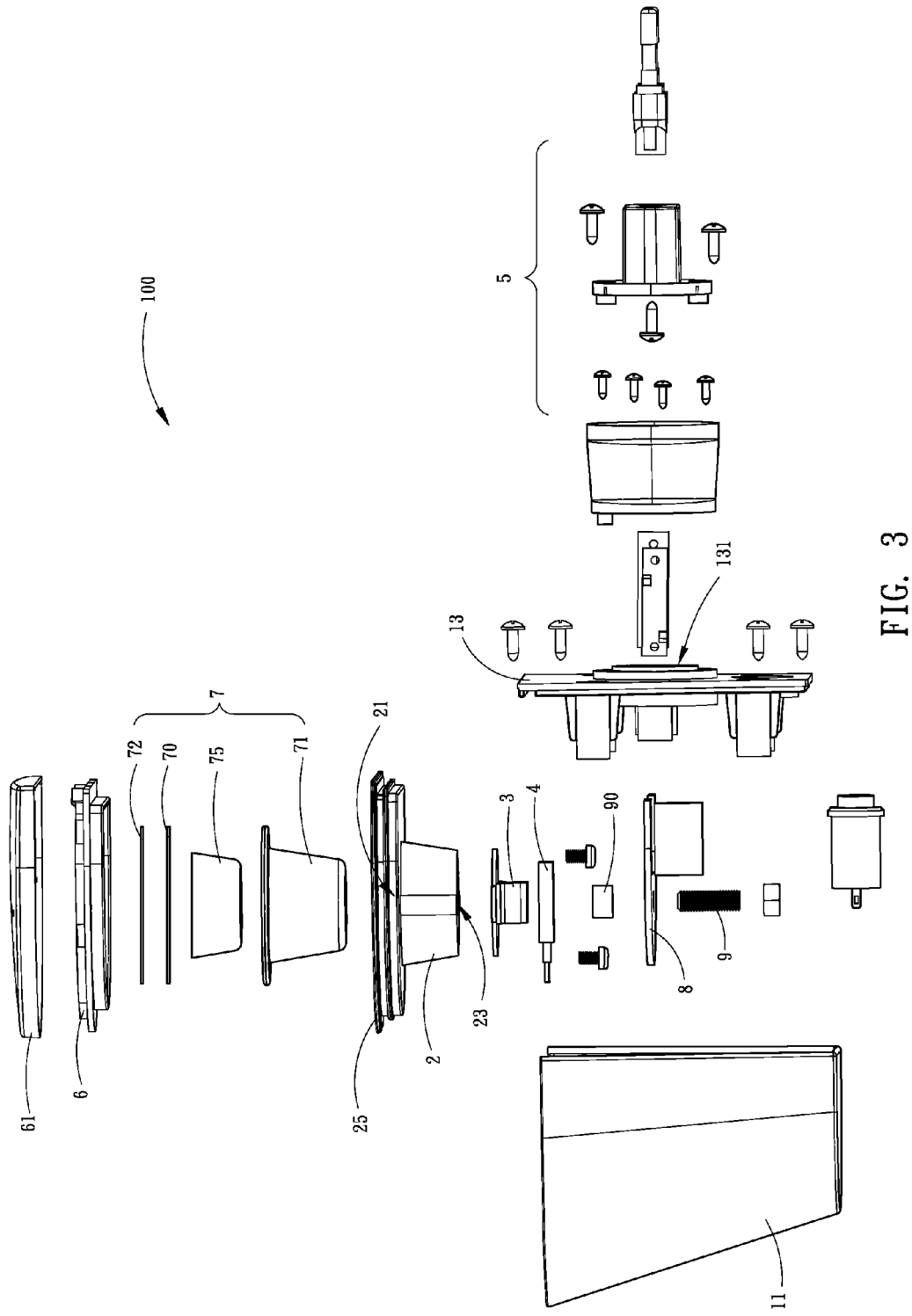
FIG. 3 is a plane exploded view of the wall socket aroma diffuser shown in FIG. 1.

Referring to FIGS. 1-3, a wall socket aroma diffuser using an aroma capsule according to the present invention comprises:

a wall socket aroma diffuser 100 including a housing 1, a receiving unit 2, a heat conducting member 3, an electrical heat source 4, and an electrical plug device 5, wherein the housing 1 has a free end 11, the receiving unit 2 has an upper opening 21 and a lower opening 23, the receiving unit 2 is coupled to the free end 11 of the housing 1, the heat conducting member 3 is coupled to the lower opening 23 of the receiving unit 21, the electrical heat source 4 is coupled to and disposed on a lower side of the heat conducting member 3, the electrical plug device 5 is disposed on one side of the housing 1, and the electrical plug device 5 is electrically connected to the electrical heat source 4; and an aroma capsule 7 received between the upper opening 21 of the receiving unit 2 and an inner side of the upper opening 21 and being in contact with the heat conducting member 3, wherein the aroma capsule 7 has a disposable container 71 and an aroma 75, the disposable container 71 has an opening 711, and the aroma 75 is received in the disposable container 71, wherein the electrical heat source 4 is connectable to a power supply, receives power supplied by the power supply, and conducts heat to the heat conducting member 3, and the heat conducting member 3 conducts the heat to the disposable container 71 and the aroma 75 for the aroma 75 to diffuse scent.

In an embodiment, the aroma 75 is an aroma block, and the aroma block is aroma wax, a scent block, a balsam block, and, preferably, is aroma wax.

In an embodiment, the electrical heat source 4 is a resistor, a metal resistor (e.g., an aluminum alloy resistor), or a cement resistor. In an embodiment, the electrical heat source is a metal resistor PTC.

In an embodiment, the aroma capsule 7 further comprises a sealing cover 72 (referring to FIG. 2) coupled to the opening 711 of the disposable container 71 for preserving the aroma 75 (e.g., aroma wax) in the aroma capsule 7 from losing its scent or being contaminated by an ambient environment. A user may easily lift off the sealing cover 72 and place the disposable container 71 of the aroma capsule 7 and the aroma 75 contained in the disposable container 71 in the upper opening 21 of the receiving unit 2, to be in contact with and heated by the heat conducting member 3.

Referring to FIGS. 2 and 3, in a preferable embodiment the aroma capsule 7 further comprises an air ventilation film 70 coupled to the opening 711 of the disposable container 71. In another embodiment, the aroma capsule 7 further comprises the above-mentioned sealing cover 72 (referring to FIG. 2). The sealing cover 72 seals the opening 711, for covering the aroma 75 and the air ventilation film 70. Therefore, the quality of the aroma 75 (aroma wax) in the aroma capsule 7 is not changed and the air ventilation film 70 is clean when the aroma capsule 7 is in storage and transportation.

Aroma is melt and evaporated to diffuse scent at about 35-75° C. In an embodiment, the aroma 75 is preferably aroma wax. Therefore, the electrical heat source 4 heats the aroma wax up to the temperature, and the aroma wax will diffuse scent into an ambient environment. Accordingly, the disposable container 71 is not melt or deformable at 35-75° C., and is made of a material that can conduct the heat generated by the electrical heat source 4 to the aroma 75. In an embodiment, the disposable container 71 is made of metal, hard plastic, or fiber bowl (including plant fiber such as corn fiber, glass fiber and carbon fiber).

In an embodiment, the disposable container 71 is an aluminum foil bowl made of metal such as foil, which is thin and light, and has a well enough heat conducting capability. The disposable container 71 can conduct the heat generated by the electrical heat source 4 to the disposable container 71 and the aroma 75 to heat the aroma 75 to diffuse scent. The aluminum-foil disposable container 71 is stiff, and is different from the brittle ceramic bowel and glass receiving unit of the prior art that are provided to contain essential oil and aroma wax.

Since the aroma 75 is placed in the disposable container 71, rather than received in the receiving unit of the prior art, a user is allowed to lift off the sealing cover 72 (referring to FIGS. 2 and 3) when using the aroma 75, without worrying about being contaminated by the aroma 75. After the aroma 75 received in the upper opening 21 of the receiving unit 2 evaporates completely, a user may remove the disposable container 71 from the upper opening 21 of the receiving unit 2 and place another aroma capsule 7 that contains aroma of different scent in the receiving unit 2, without the need of cleaning the disposable container 71. Since the disposable container 71 is made of aluminum foil, a user does not need to worry about breaking the disposable container 71. Since the disposable container 71 is disposable, the user does not need to wash the disposable container 71 or provide a certain receiving unit to contain the aroma 75.

In an embodiment, the air ventilation film 70 has a plurality of air vents for guiding the scent of the aroma 75 (aroma wax) upward into an ambient environment. In another embodiment, the air ventilation film 70 is a fabric (e.g., a non-woven fabric, fiber fabric, linen and canvas), fiber sheet, porous plastic film, or porous metal foil. The user of the aroma capsule 7 is allowed to lift off the sealing cover 72 and place the disposable container 71 in the receiving unit 2. The electrical heat source 4 heats the aroma capsule 7 and makes the aroma 75 to diffuse scent. As the wall socket aroma diffuser 100 using an aroma capsule according to the present invention is toppled by chance, the aroma wax in the disposable container 71 is prevented by the air ventilation film 70 from flowing and being in contact with the electrical heat source 4. Therefore, the wall socket aroma diffuser according to the present invention is safe to use and will not pollute the environment.

Figure 4:
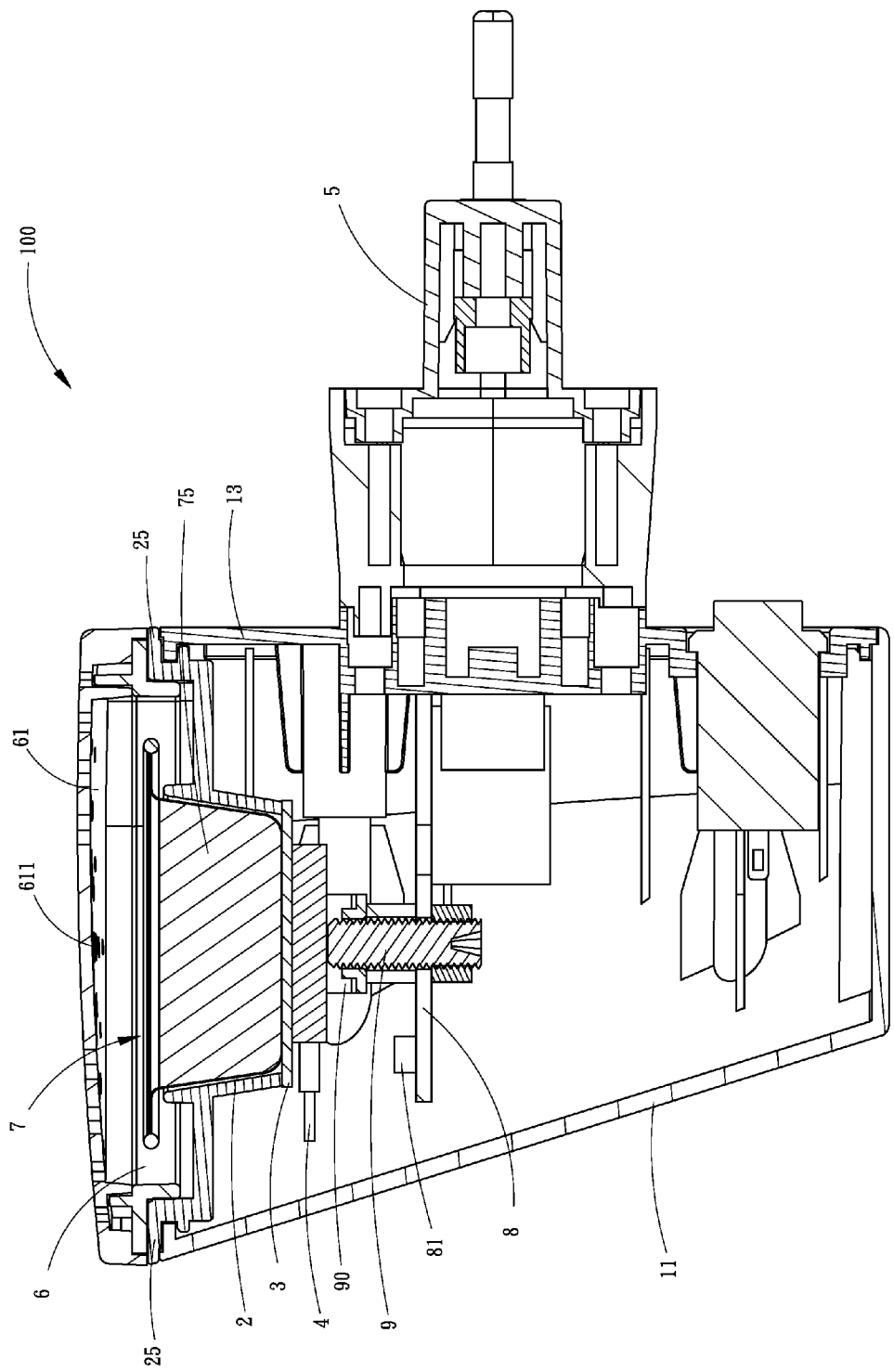
FIG. 4 is a cross-section view of the wall socket aroma diffuser shown in FIG. 1.

As shown in FIGS. 2-4, in an embodiment the wall socket aroma diffuser 100 further comprises a printed circuit board (PCB) 8 coupled in the housing 1, and the PCB 8 is further coupled to a light emitting diode (LED) 81. In an embodiment, the receiving unit 2 is made of a transparent material, such as transparent or translucent, colorful or partially colorful plastic or glass, and acts as a light guiding member that forms color. The receiving unit 2 further comprises a light guiding flange 25 extending around an outer rim of the receiving unit 2 and protrusively disposed on an upper side of the free end 11 of the housing 1. The PCB 8 is connected to a power supply that supplies power to the LED 81, and the LED emits and projects light onto the transparent receiving unit 2. The light is guided and diffused by the receiving unit 2 and becomes non-harsh light. The light guiding flange 25 displays the color onto an outer side of the wall socket aroma diffuser 100, to please people's eyes and act as a night light. The wall socket aroma diffuser thus brings temperament and interest to people's daily life. The PCB 8 intermittently provides power to the electrical heat source 4 and the LED 81. Accordingly, the electrical heat source 4 can save power intermittently and stay at a low temperature. The LED 81 also emit light intermittently, and can be used as a night lamp.

Referring to FIGS. 2-4, in an embodiment the wall socket aroma diffuser 100 further comprises a screw rod 9 and a thermal insulation assembly 90, and the PCB 8 has a hole 83. The thermal insulation assembly 90 is coupled to an outer rim of one side of the screw rod 9 and props against under the electrical heat source 4. The other side of the screw rod 9 passes under the hole 83 of the PCB 8 and is fixed by a screw. Therefore, the thermal insulation assembly 90 is isolated from the heat generated by the electrical heat source 4 and does not conduct the heat to the PCB 8.

In an embodiment, the wall socket aroma diffuser 100 further comprises a hollow frame 6 and a cover 61. The cover 61 has apertures 611 for diffusing scent. The hollow frame 6 is coupled to an upper side of the light guiding flange 25 above the free end 11 of the housing 1. The cover 61 is coupled to an upper side of the hollow frame 6 for covering the aroma at the inner side of the free end 11 of the housing 1. The aroma diffuses scent through the hollow frame 6 and the apertures 611 of the cover 61 to the ambient environment.

In an embodiment, the electrical plug device 5 is a swing plug device, and the swing plug device is coupled to one side of the housing 1. The swing plug device is electrically connected to the PCB 8. The swing plug device can cooperate with an electrical socket toward any direction, and the aroma capsule 7 can diffuse scent upward through the apertures 611 of the cover 61.

In an embodiment, the housing 1 comprises a front housing 10 and a rear housing 13. The rear housing 13 is a board member, and the board member has a hole 131. The swing plug device is coupled to the hole 131. The front housing 10 comprises the free end 11 and a lateral opening 15 perpendicular to the free end 11. The rear housing 13 is coupled to the lateral opening 15 of the front housing 10.

The upper opening 21 of the receiving unit 2 is sizable with respect to the aroma capsule 7, and the aroma capsule 7 can be received in the upper opening 21 of the receiving unit 2 securely.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A wall socket aroma diffuser device, comprising:
a wall socket aroma diffuser including a housing, a receiving unit, a heat conducting member, an electrical heat source, and an electrical plug device, wherein the housing has a free end, the receiving unit is coupled to the free end of the housing and has an upper opening and a lower opening opposite to the upper opening, the heat conducting member is coupled to the lower opening of the receiving unit, the electrical heat source is coupled to and disposed on a lower side of the heat conducting member, the electrical plug device is disposed on a lateral side of the housing, and the electrical plug device is electrically connected to the electrical heat source; and
an aroma capsule received in the receiving unit from the upper opening, having a bottom in contact with the heat conducting member, wherein the aroma capsule has a disposable container and aroma, the disposable container has the bottom and an opening opposite to the bottom, and the aroma is received in the disposable container,
wherein the electrical heat source is electrically connected to a power supply and generates and conducts heat to the heat conducting member, and the heat conducting member conducts the heat to the disposable container and the aroma for the aroma to diffuse scent, thereby a user just needs to remove the disposable container from the upper opening of the receiving unit and place a new aroma capsule, instead of cleaning the disposable container for new aroma.

2. The wall socket aroma diffuser of claim 1, wherein the aroma capsule further comprises an air ventilation film coupled with the opening of the disposable container, and a sealing cover covering on the air ventilation film to seal the opening, so that the quality of the aroma in the aroma capsule is not changed and the air ventilation film is clean when the aroma capsule is in storage and transportation.

3. The wall socket aroma diffuser of claim 2, wherein the air ventilation film is a fabric, a fiber sheet or an air ventilation film made of a porous plastic film or a porous metal foil.

4. The wall socket aroma diffuser of claim 1, wherein the aroma is aroma wax.

5. The wall socket aroma diffuser of claim 1, wherein the disposable container is made of metal, hard plastic, fiber bowl or a composite material.

6. The wall socket aroma diffuser of claim 5, wherein the disposable container is made of metal and is an aluminum foil bowl.

7. The wall socket aroma diffuser of claim 1, wherein the wall socket aroma diffuser further comprises a printed circuit board (PCB) coupled to an inside of the housing and a light emitting diode (LED), the receiving unit is made of a transparent material and has a light guiding flange extending around an outer rim of the receiving unit, the light guiding flange is protrusively disposed on an upper side of the free end of the housing, the PCB is located at a lower side of the electric heat source and connected to a power supply that supplies power to the LED, the LED emits and projects light onto the transparent receiving unit, the light is guided and diffused by the receiving unit to generate color, and the color is displayed via the light guiding flange onto the outer side of the wall socket aroma diffuser.

8. The wall socket aroma diffuser of claim 7, wherein the wall socket aroma diffuser further comprises a screw rod with a first distal end secured in the electrical heat source and a thermal insulation assembly, the PCB has a hole, the thermal insulation assembly is coupled to an outer rim of one side with the first distal end of the screw rod and props against under the electrical heat source, and the other side of the screw rod passes downward the hole of the PCB and is fixed by a nut at a second distal end opposite to the first distal end, so that the thermal insulation assembly is sandwiched between the electrical heat source and the PCB, and the thermal insulation assembly isolates the heat of the electrical heat source from being conducted to the PCB.

9. The wall socket aroma diffuser of claim 8, wherein the electrical plug device is a swing plug device, and the swing plug device is electrically connected to the PCB.

10. The wall socket aroma diffuser of claim 7, wherein the electrical plug device is a swing plug device, and the swing plug device is electrically connected to the PCB.

11. The wall socket aroma diffuser of claim 10, wherein the housing comprises a front housing and a rear housing, the rear housing has a hole, the swing plug device is coupled to the hole of the rear housing, the front housing comprises the free end and a lateral opening perpendicular to the free end, and the rear housing is coupled to the lateral opening of the front housing.

12. The wall socket aroma diffuser of claim 7, wherein the wall socket aroma diffuser further comprises a hollow frame and a cover, the cover has an aperture, the hollow frame is coupled to an upper side of the light guiding flange above the free end of the housing, and the cover is coupled to an upper side of the hollow frame.

\* \* \* \* \*